United States Patent [19]

Silva

[11] Patent Number: 5,363,840
[45] Date of Patent: Nov. 15, 1994

[54] PARALLEL LARYNGOSCOPE WITH ACCESS OPENING

[76] Inventor: Rafael E. Silva, 812 Glenridge Dr., Edmond, Okla. 73013

[21] Appl. No.: 192,236

[22] Filed: Feb. 4, 1994

[51] Int. Cl.$^5$ ............................................. A61B 1/06
[52] U.S. Cl. ........................................ 128/11; 128/13
[58] Field of Search ............................. 128/10, 11–19; 354/132, 126

[56] References Cited

U.S. PATENT DOCUMENTS

| | | | |
|---|---|---|---|
| D. 312,500 | 11/1990 | Abadir | D24/18 |
| 218,055 | 7/1897 | Nitze . | |
| 1,042,133 | 10/1912 | Marshall . | |
| 1,240,320 | 9/1917 | Dameron . | |
| 1,246,338 | 11/1917 | Smit . | |
| 1,319,904 | 10/1919 | Roberts . | |
| 1,364,873 | 1/1921 | Fitzgerald . | |
| 1,374,984 | 4/1921 | Cameron . | |
| 1,388,170 | 8/1921 | Cameron . | |
| 1,504,343 | 8/1924 | Heard . | |
| 1,510,304 | 9/1924 | Cameron . | |
| 2,630,114 | 3/1953 | Hart | 128/11 |
| 2,756,742 | 7/1956 | Barton | 128/15 |
| 3,964,488 | 6/1976 | Ring et al. | 128/351 |
| 4,320,745 | 3/1982 | Bhitiyakul et al. | 128/11 |
| 4,337,761 | 7/1982 | Upsher | 128/1 |
| 4,360,008 | 11/1982 | Corazzelli, Jr. | 128/11 |
| 4,377,164 | 3/1983 | Sabbota | 128/207.14 |
| 4,574,784 | 3/1986 | Soloway | 128/11 |
| 4,799,485 | 1/1989 | Furey et al. | 128/11 |
| 4,866,465 | 9/1989 | Gallegos | 354/126 |
| 5,024,218 | 6/1991 | Ovassapian et al. | 128/200.26 |
| 5,092,314 | 3/1992 | Zeitels | 128/10 |
| 5,178,132 | 1/1993 | Mahefky | 128/17 |

OTHER PUBLICATIONS

"Instrumental Aids to Bronchoscopy and Esophagoscopy," by Dr. Chevalier Jackson, 1907, source not indicated, 1907 (pp. 492–494).
"Intra-Tracheal Anesthesia from the Standpoint of the Nose, Throat and Oral Surgeon With a Description of a New Instrument for Catheterizing the Trachea," by Dr. Henry H. Janeway, source not indicated, 1913, (pp. 1082–1090).
"New Inventions, An Improved Laryngoscope for Anesthetists," by I. W. Magill, *The Lancet*, Mar. 6, 1926 (p. 500).
"Exposure and Illumination of the Pharynx and Larynx by the General Practitioner," by Dr. Paluel Flagg, *Archives of Otolaryngology*, 1928 (pp. 716–717).
"Technique in Endotracheal Anaesthesia," by I. W. Magill, *The British Medical Journal*, Nov. 15, 1930 (pp. 817–819).
"New Inventions, A Detachable Laryngoscope," by John Elam, *The Lancet*, Sep. 14, 1935 (p. 616).
"A New Laryngoscope," by Dr. Robert A. Miller, source not indicated, May, 1941 (pp. 317–320).
"Preparations and Appliances, An Improved Laryngoscope," by Prof. R. R. MacIntosh, *British Medical Journal*, Dec. 27, 1941 (p. 914).
"Advantages of a Curved Laryngoscope," by Dr. W. H. Cassels, *Current Comment and Case Reports*, 1942 (pp. 580–582).

(List continued on next page.)

*Primary Examiner*—Stephen R. Crow
*Assistant Examiner*—Donna J. Maraglio
*Attorney, Agent, or Firm*—Dunlap, Codding & Lee

[57] ABSTRACT

A parallel laryngoscope with an access opening in the connecting member between the blade and the handle that permits manipulation of the tongue and avoids pressure on the lower teeth during intubation. The connecting member is removably connected to the handle in the conventional "hook-on" type manner, and the same hook-on connection may be provided between the connecting member and the blade. Due to the conventional connectors, the components of this improved laryngoscope can be assembled quickly and is used in the conventional manner. No additional training of personnel is necessary. Moreover, the components are completely interchangeable and can be disassembled for convenient storage.

20 Claims, 3 Drawing Sheets

OTHER PUBLICATIONS

"New Inventions, A New Laryngoscope," by Dr. R. R. MacIntosh, *The Lancet*, Feb. 13, 1943, (p. 205).

"A New Modification of the Conventional Laryngoscope and Tehnic for Laryngoscopy", by Dr. Signey C. Wiggin, *Anesthesiology*, vol. 5, Jan. 1944 (pp. 61–68).

"Direct Laryngoscopy and Tracheal Intubation," by Banniser and Macbeth, *The Lancet*, Nov. 18, 1944, (pp. 651–654).

"Awake Intubation," by J. L. Thomas, *Anaesthesia*, vol. 24, No. 1, Jan., 1969 (pp. 28–35).

"Transctrachael Ventilation," by Spoerel, Narayanan and Singh, *British Journal of Anaesthesia*, 1971 (pp. 932–939).

"Awake Endotracheal Intubation: A Review of 267 Cases," by Kopman, Wollman, Ross and Surks, *Anesthesia and Analgesia*, vol. 54, No. 3, May–Jun., 1975, (pp. 323–327).

"Transtracheal Ventilation," by Attia, Battit and Murphy, *JAMA*, vol. 234, No. 11, Dec. 15, 1975 (pp. 1152–1153).

"Endotracheal Intubation and Treacher-Collins Syndrome," by Sklar and King, *Anesthesiology*, vol. 44, No. 3, Mar., 1976 (pp. 247–249).

"A Simple Connector for Transtracheal Ventilation," by Dr. Thomas W. Stinson, *Anesthesiology*, vol. 47, No. 1977 (p. 232).

"A Systemic Approach to the Difficult Intubation," Dr. Richard Ament, *Anesthesiology Review*, vol. V, No. 7, Jul., 1978 (pp. 12–16).

"Mechanical Problems of the Airway," by Lopez and James, *Clinical Anesthesia*, Chapter 1, date unknown (pp. 8–22).

Brochure showing Cricothyrotomy Kit, Omnicon Medical, date unknown.

Brochure, Anesthesia Associates, Inc., 1993, showing various instruments.

Brochure, "The Laryngoscope Collection," Welch Allyn, date unknown.

"An Improved Laryngoscope for Use with Operating Microscope", Busby, *Arch Otolaryng.*, vol. 91, Feb. 1970, p. 195.

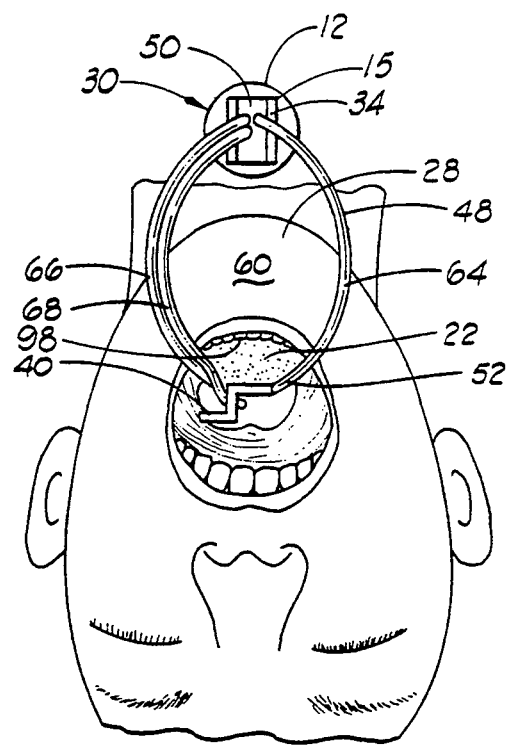
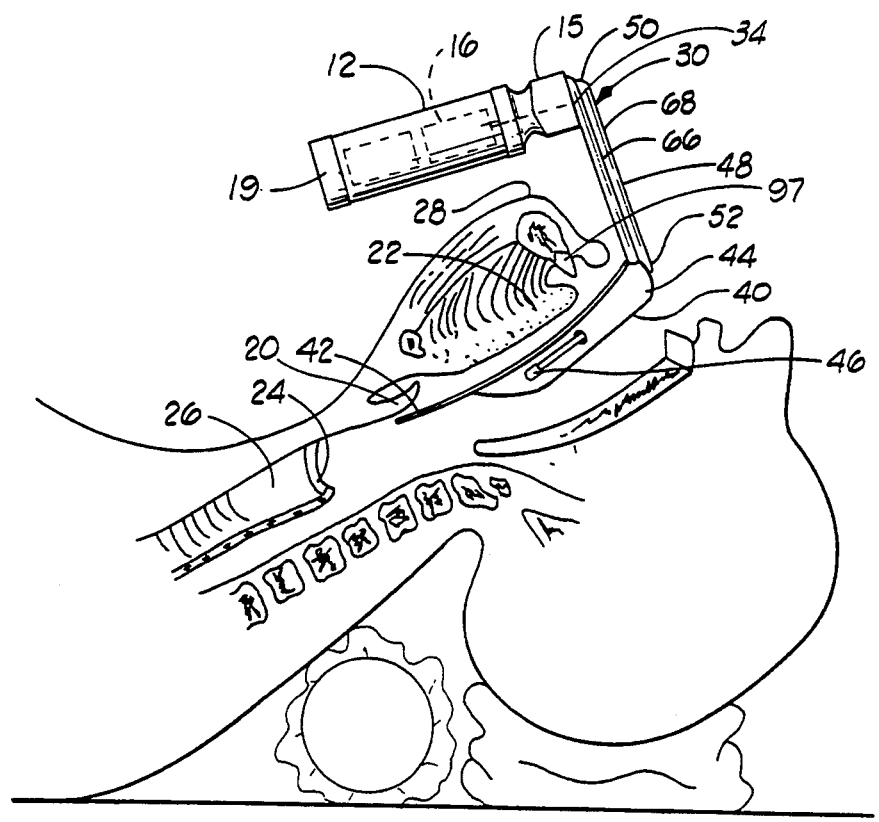
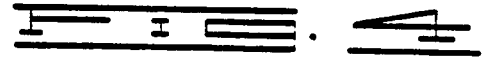

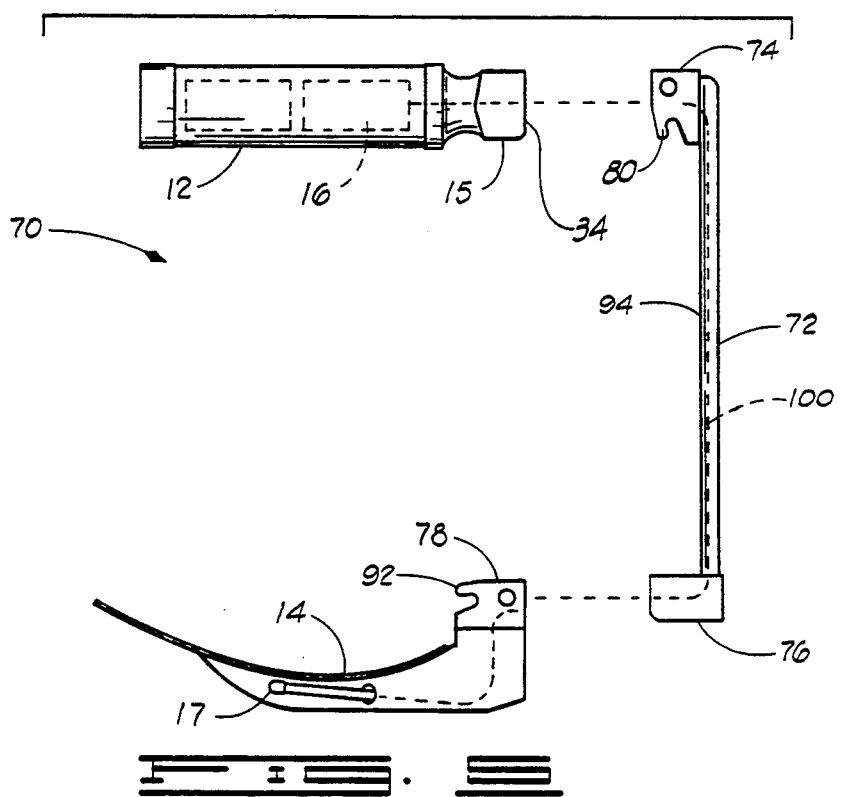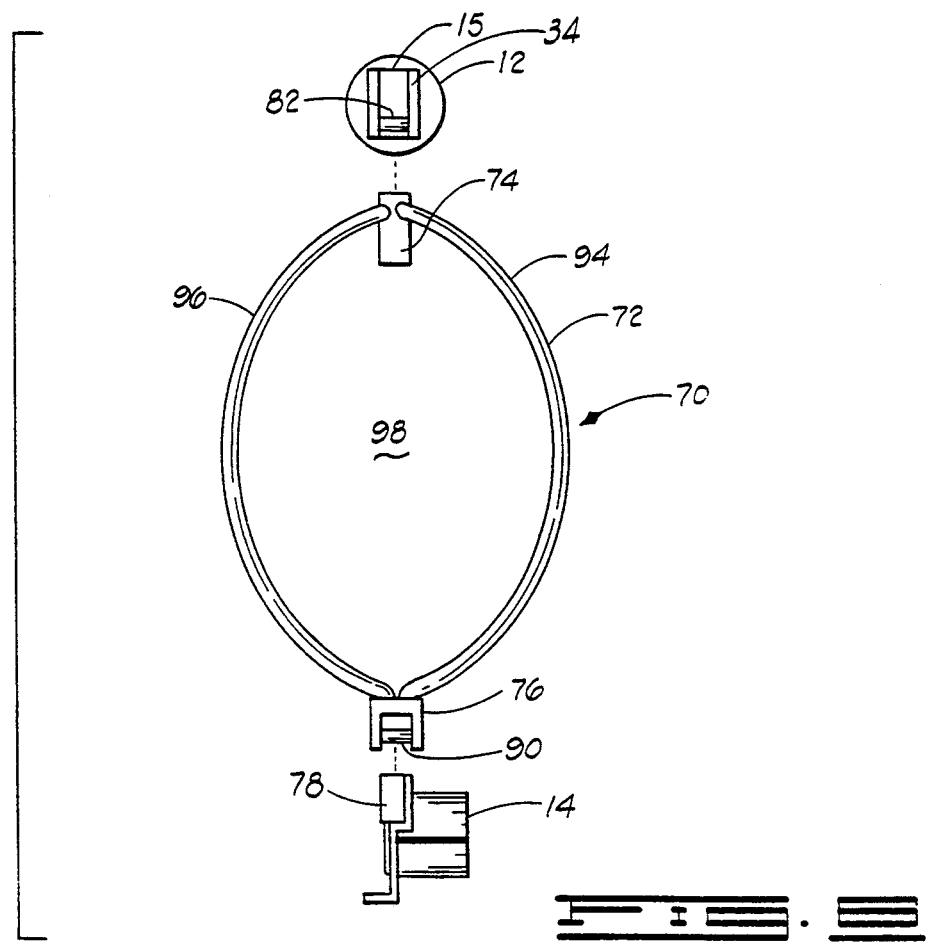

PARALLEL LARYNGOSCOPE WITH ACCESS OPENING

FIELD OF THE INVENTION

The present invention relates generally to laryngoscopes.

BRIEF DESCRIPTION OF THE DRAWINGS

FIG. 3 is a front elevational view of the parallel laryngoscope of the present invention inserted in the mouth of a patient.

FIG. 4 is a side elevational view of the parallel laryngoscope shown in FIG. 3 with the head of the patient shown in section.

FIG. 5 is an exploded side elevational view of another embodiment of the laryngoscope of the present invention.

FIG. 6 is an exploded front elevational view of the embodiment shown in FIG. 5.

DETAILED DESCRIPTION OF THE PREFERRED EMBODIMENTS

Laryngoscopes are used in many medical procedures to facilitate access to the airway in a patient. Damage to oral and pharyngeal structures is always a risk during such procedures. This is particularly true during procedures performed on an emergency basis.

Figure 1:
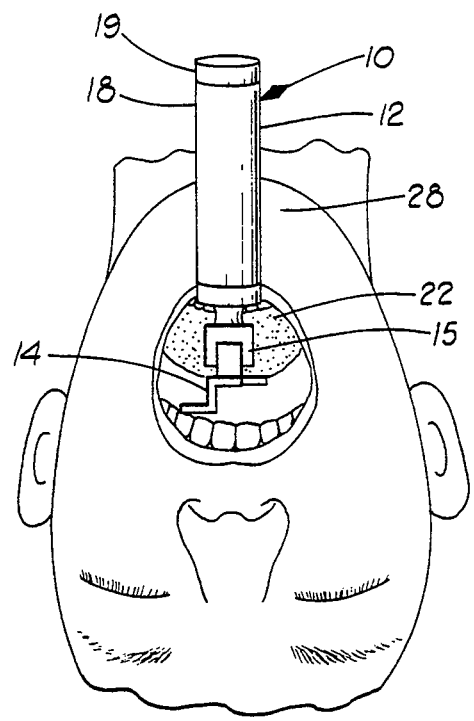
FIG. 1 is a front elevational view of a prior art device shown inserted in the mouth of a patient.
Figure 2:
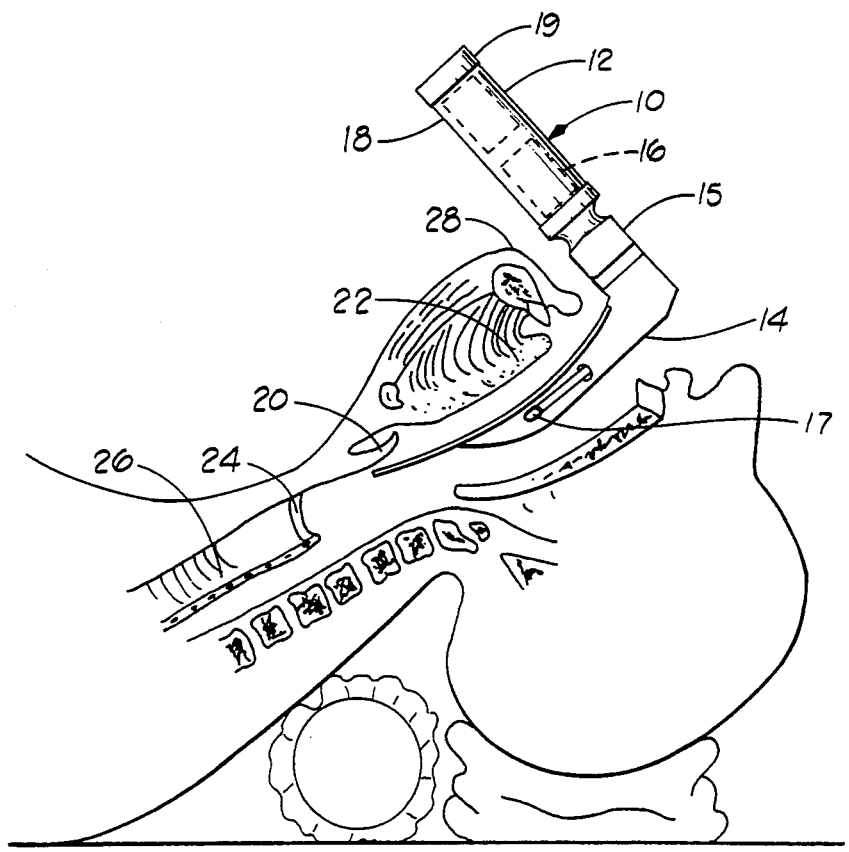
FIG. 2 is a side view of the prior art device shown in FIG. 1 with the head of the patient shown in section.

The most popular type of conventional laryngoscope presently in use is exemplified by the laryngoscope depicted in FIGS. 1 and 2 of the drawings, to which reference now is made. The laryngoscope 10 comprises a handle 12 and a blade 14. The blade 14 is removably connected to the handle 12 by means of a "hook-on" type connection at the end 15 of the handle. Batteries 16 housed in the handle 12 supply power to a light source 17 supported near the tip of the blade 14. The second end 18 of the handle 12 has a removable cap 19 which permits access to the battery cavity.

The connection between the blade 14 and the handle 12 permits the blade to be moved pivotally between a collapsed position to an operative position. In the operative position, the blade 14 extends generally perpendicular to the handle 12. In this position, an electrical connection is made between the blade 14 and the handle 12 so that the light source 17 is activated. In the collapsed position (not shown), the blade 14 is connected to the handle 12 but hangs downwardly alongside it and no electrical contact is made so that the light 17 is deactivated.

A large variety of hook-on type blades are commercially available. Likewise, several sizes and shapes of handles are available. Because of the universal hook-on connection, the handles and blades are interchangeable providing convenience and versatility with minimal cost.

With continuing reference to FIGS. 1 and 2, the use of the conventional laryngoscope 10 is illustrated and will be summarized herein only briefly. First, the blade 14 is connected to the handle 12 and moved to the operative position. Next, the patient is placed in a supine position with the neck flexed and the head extended. Then, holding the handle 12 so that the blade 14 is below it, the blade is inserted into the mouth. The tip of the blade 14 is guided to expose the epiglottis 20 and position it so that entrance through the glottis is permitted. In many cases, the tip of the blade 14 is positioned to press the epiglottis 20 up against the base of the tongue 22. An open path through the larynx 24 and into the trachea 26 then is provided by manipulating the lower jaw 28 and tongue 22 with the blade 14 by gently lifting the handle 12.

Now it will be appreciated that damage to tissues and structures in the mouth and throat can occur easily during the manipulation of the laryngoscope. This is especially true under stressful emergency situations or where intubation is complicated by bleeding or damaged structures.

Moreover, the lever-like shape of the laryngoscope 10 with its perpendicular blade 14 increases the likelihood of injury. This is because even a gentle pivotal movement of the handle 12, translates into a much stronger force at the end of the blade 14 against the tissues. Consequently, great care must be exercised when lifting and positioning the handle so as not to exert undue force against the lower jaw 28, tongue 22 and the surrounding structures.

It will also be appreciated that proper positioning of the epiglottis 20 often can be facilitated by manipulation of the tongue 22. However, as illustrated best in FIG. 1, when the laryngoscope is in place access to the tip of the tongue 22 is obstructed by the end 15 of the handle 12. It is difficult if not impossible to pull the tongue 22 directly upward or cephalically, that is, away from the larynx, as is sometimes necessary.

The present invention provides an improved laryngoscope which reduces the likelihood of injury and facilitates the intubation procedure. The laryngoscope of the present invention includes a connecting member which supports the blade generally parallel to the handle, rather than perpendicular to it. This eliminates or greatly reduces the hazardous lever effect. Further, the connecting portion provides an access opening between the end of the blade and the handle. Through this access opening, the tip of the tongue can be grasped and manipulated in a manner not permitted by conventional laryngoscopes, as illustrated by FIG. 3. These and other advantages will be apparent from the following description of the preferred embodiments of the present invention.

With reference now to FIGS. 3 and 4, a first embodiment of the present invention is depicted and designated generally by the reference numeral 30. Like the prior art laryngoscope 10 in FIGS. 1 and 2, the laryngoscope 30 comprises a conventional handle 12.

The laryngoscope 30 further comprises a blade 40. The blade 40 may be of any size and shape but generally will have a first end 42 and a second end 44. The first end 42 defines a tip which preferably is illuminated by a light source 46 supported on the blade in a conventional manner.

To provide parallel positioning of the blade 40 relative to the handle 12, the laryngoscope includes a connecting member 48 between the blade and the handle. The connecting member 48 has a first end 50 and a second end 52. The first end 50 is equipped with the hook or male portion of the hook-on type connection for removably mating with the second end 34 of the handle 12. The second end 52 of the connecting member 48 is affixed rigidly to the second end 44 of the blade 40.

As seen in FIG. 3, the connecting member 48 provides an access opening 60 between the blade 40 and the handle 12. While the access opening 60 may vary in size and shape, it should permit access to the tip of the tongue 22 therethrough for the reasons described hereinabove. Moreover, it should be wide enough to be positioned lateral to the lower teeth when the blade is inserted in the mouth for a reason yet to be described.

In the preferred embodiment, the connecting member 48 comprises first and second opposing tubular members 64 and 66 which define a generally oval access opening 60. The first and second tubular members 64 and 66 may be made of stainless steel or some other suitable material which will be sturdy, durable and capable of withstanding sterilization techniques. A third tubular member 68 may be provided for carrying the wiring for the light source.

As illustrated in FIGS. 3 and 4, the access opening 60 permits access to the tip of the tongue 22 during the procedure. As discussed above, manipulation of the tongue 22 sometimes is necessary in order to position the epiglottis 20 properly.

The access opening 60 has yet another advantage not offered by conventional laryngoscopes. As shown in FIGS. 1 and 2, caudal movement of the blade 14 on a conventional handle 12 is limited by the end 15 of the handle; the blade cannot be moved caudally beyond the point where the lower end of the handle abuts the lower teeth 97 and jaw 28. If the blade 14 is not long enough to extend to the epiglottis 20, it often is necessary to change the blade to a longer one. Because of the access opening 60 in the connecting member 48 of the present invention, the teeth 98 do not block caudal movement of the blade 40, as illustrated in FIGS. 3 and 4. Thus, the range of caudo-cephalic movement of the blade 40 is greater than in the conventional laryngoscope 10 (FIGS. 1 and 2). This allows use of fewer blade sizes and reduces the likelihood that a blade change will be required during the procedure.

Turning now to FIGS. 5 and 6, there is shown therein a second preferred embodiment of the present invention which is designated generally by the reference numeral 70. The laryngoscope 70 comprises a handle and a blade such as the conventional handle 12 and blade 14 in the prior art device of FIGS. 1 and 2.

The laryngoscope 70 further comprises a connecting member 72 having a first end 74 and second end 76. As in the embodiment of FIGS. 3 and 4, the first end 74 is provided with a male portion 80 (FIG. 5) of a conventional hook-on type connection for mating with the second end 15 of the handle 12 having the female or cross-bar portion 82 (FIG. 6) of the connection.

The second end 76 of the connecting member 72 is provided with a cross-bar 90 (FIG. 6) for matingly receiving the hook 92 (FIG. 5) on the connecting end 78 of the blade 14. The use of the hook-on type connections is advantageous because it is well known to practitioners who routinely use laryngoscopes. Thus, the operation of this invention will be readily apparent, and no additional training in the assembly of the device will be required.

Of course, the hook-on type connections have other advantages. The laryngoscope 30 can be assembled very quickly, which is important in emergencies, and can be stored conveniently in the disassembled form. Still further, as discussed hereinabove, this universal connection provides economy and versatility through the interchangeability of components. Nevertheless, it will be appreciated that, while the hook-on type connections are preferred, other types of connections may be employed.

Referring still to FIGS. 5 and 6, the connecting member 72 of this embodiment is entirely separate from the blade 14 and handle 12. Accordingly, the connecting member 72 can be used with any combination of conventional handles and blades.

The connecting member 72 comprises first and second arched tubular members 94 and 96 which define an oval access opening 98 similar to the access opening 60 in the connecting member 48 of the embodiment shown in FIGS. 3 and 4. The access opening 98 of the connecting member 72 in the embodiment of FIGS. 5 and 6 operates similarly to provide the same advantages as discussed above in connection with the embodiment of FIGS. 3 and 4. In this embodiment, wiring 100 (shown in phantom in FIG. 5) for the circuit between the batteries 16 and light source 17 is channeled through the tubular members 94 or 96 or both.

Changes may be made in the combination and arrangement of the various parts, elements, steps and procedures described herein without departing from the spirit and scope of the invention as defined in the following claims.

What is claimed is:

1. A laryngoscope for accessing the trachea of a patient through the glottis, comprising:
   a blade;
   a handle;
   a connecting member extending between the blade and the handle and having a first end connected to the blade and a second end connected to the handle thereby supporting the handle generally parallel to the blade, the connecting member including an access opening between the first end and the second end, the access opening being shaped to permit manipulation of the tip of the tongue and to avoid the lower teeth during use of the laryngoscope.

2. The laryngoscope of claim 1 wherein the blade is removably connected to the connecting member.

3. The laryngoscope of claim 1 wherein the connecting member is removably connected to the handle.

4. The laryngoscope of claim 1 wherein the blade includes a light.

5. The laryngoscope of claim 4 further comprising a power source for activating the light, the power source comprising a battery housed in the handle.

6. The laryngoscope of claim 1 wherein the blade is removably connected to the connecting member and wherein the connecting member is removably connected to the handle.

7. The laryngoscope of claim 6 further comprising:
   a first hook connecting means at the first end of the connecting member for permitting the passage of electrical current between the first end and the blade;
   second hook connecting means at the second end of the connecting member for permitting the passage of electrical current between the second end and the handle; and
   electrical conductor means extending between the first and second hook connecting means for permitting the passage of electrical current through the connecting member.

8. The laryngoscope of claim 1 wherein the first end of the connecting member is removably connectable to the handle, and further comprising first and second opposing tubular members extending between the first and second ends, which tubular members define the access opening.

9. The laryngoscope of claim 8 wherein the access opening is generally oval in shape.

10. The laryngoscope of claim 8 further comprising a light on the blade, a battery housed in the handle and an electrical conductor means extending between the battery and the light for permitting the passage of electrical current therebetween.

11. The laryngoscope of claim 10 wherein the electrical conductor means is contained within at least one of the first and second opposing tubular members of the connecting member.

12. The laryngoscope of claim 8 wherein the second end of the connecting member is removably connectable to the blade.

13. The laryngoscope of claim 1 wherein the access opening is generally oval in shape.

14. A laryngoscope connecting member for removably connecting a laryngoscope handle and a laryngoscope wherein the laryngoscope handle and the laryngoscope blade have interconnecting hook connector means, wherein the laryngoscope blade includes a light, and wherein the laryngoscope handle comprises a housing for a battery to activate the light, the laryngoscope connecting member comprising:

a first end comprising a hook connector means for removably connecting the first end to the hook connector means on the laryngoscope blade and for providing an electrical connection therebetween when the hook connector means on the first end of the connecting member is connected to the hook connector means on the laryngoscope blade;

a second end comprising a hook connector means for removably connecting the second end to the hook connecting means on the laryngoscope handle and for providing an electrical connection therebetween when the hook connector means on the second end is connected to the hook connector means on the laryngoscope handle;

a body portion extending between the first and second ends shaped to support the laryngoscope blade generally parallel to the laryngoscope handle when the connecting member is connected to the laryngoscope blade and the laryngoscope handle, the body portion including an access opening between the first end and the second end, the access opening being shaped and sized to permit manipulation of the tip of the tongue and to avoid the lower teeth during use of the laryngoscope, the body portion further including electrical conductor means for permitting the passage of electrical current from a battery housed in the handle to the blade.

15. The laryngoscope connecting member of claim 14 wherein the access opening is generally oval in shape.

16. The laryngoscope connecting member of claim 16 wherein the body portion comprises first and second opposing tubular members extending between the first and second ends, which tubular members define the access opening.

17. The laryngoscope connecting member of claim 16 wherein the access opening is generally oval in shape.

18. A laryngoscope blade for use with a laryngoscope handle, which handle has a hook connector means for connecting the laryngoscope handle to the laryngoscope blade, the laryngoscope handle having a housing for containing a battery and including electrical conductor means for permitting passage of electrical current between the battery in the housing to the hook connector means, the laryngoscope blade comprising:

a blade portion having a first end and a second end;

a light at the first end of the blade;

a connecting portion having a first end and a second end, the first end extending from the second end of the blade portion, the second end of the connecting portion comprising a hook connector means for connecting to the hook connector means on the laryngoscope handle, the hook connector means on the connecting portion including means for permitting the passage of electrical current between the hook connector means on the laryngoscope handle and hook connector means on the laryngoecope blade, the connecting portion including electrical conductor means for permitting the passage of electrical current between the light on the blade portion and the hook connector means on the second end of the connecting portion, and the connecting portion being shaped and sized to support the blade portion generally parallel to the laryngoscope handle when the laryngoscope blade is connected to the laryngoscope handle, and the connecting portion further including an access opening extending between the first and second ends and shaped and sized to permit manipulation of the tip of the tongue and to avoid the lower teeth during use of the laryngoscope blade.

19. The laryngoscope blade of claim 18 wherein the connection portion comprises a pair of opposing tubular members extending between the first and second ends, said tubular members defining the access opening.

20. The laryngoscope blade of claim 18 wherein the access opening is generally oval in shape.

* * * * *